(12) United States Patent
Gillies et al.

(10) Patent No.: US 9,131,205 B2
(45) Date of Patent: Sep. 8, 2015

(54) SYSTEM AND METHOD FOR DISTRACTION OF PATIENT DURING SCANNING

(75) Inventors: Murray Fulton Gillies, Eindhoven (NL); Raymond Van Ee, Geldrop (NL); Gijs Antonius Franciscus Van Elswijk, Eindhoven (NL); Tim Johannes Willem Tijs, Helmond (NL)

(73) Assignee: Koninklijke Philips N.V., Eindhoven (NL)

( * ) Notice: Subject to any disclaimer, the term of this patent is extended or adjusted under 35 U.S.C. 154(b) by 178 days.

(21) Appl. No.: 13/988,538

(22) PCT Filed: Nov. 21, 2011

(86) PCT No.: PCT/IB2011/055207
§ 371 (c)(1),
(2), (4) Date: May 21, 2013

(87) PCT Pub. No.: WO2012/069979
PCT Pub. Date: May 31, 2012

(65) Prior Publication Data
US 2013/0245364 A1     Sep. 19, 2013

(51) Int. Cl.
*H04N 9/87* (2006.01)
*A61M 21/02* (2006.01)
(Continued)

(52) U.S. Cl.
CPC *H04N 9/87* (2013.01); *A61B 5/055* (2013.01); *A61B 5/742* (2013.01); *A61B 5/7405* (2013.01);
(Continued)

(58) Field of Classification Search
CPC ...... A61B 5/055; A61B 5/7405; A61B 5/742; A61M 2021/0016; A61M 2021/0022; A61M 2021/0027; A61M 2021/005; A61M 21/02; A61M 2205/3375; G01R 33/283; G01R 33/288; H04N 9/87

USPC ............. 600/28, 409, 410, 418, 427; 40/436, 40/438; 345/8; 381/73.1; 348/738

See application file for complete search history.

(56) References Cited

U.S. PATENT DOCUMENTS 5,877,732 A    3/1999   Ziarati
7,823,306 B1   11/2010  Kersten et al.

FOREIGN PATENT DOCUMENTS

| DE | 10237924 | 3/2004 |
|---|---|---|
| WO | WO2005051471 | 6/2005 |
| WO | WO2010018534 | 2/2010 |
| WO | WO2010105153 | 9/2010 |
| WO | WO2010108105 | 9/2010 |

OTHER PUBLICATIONS

Van Ee et al. (2009). Multisensory Congruency as a Mechanism for Attentional Control over Perceptual Selection. Journal of Neuroscience 29(37):11641-11649.

(Continued)

*Primary Examiner* — Michael Rozanski (57) ABSTRACT

A system and method for reducing anxiety of a patient during medical scanning in a medical scanner which may produce significant levels of acoustic noise. A processor or control unit receives a measure of variation in a parameter of the scanner noise during the medical scanning. The processor then generates outputs to audio and video playback units that present an audio-video scenery to the patient during the scanning in accordance with the measure of variation in the parameter of the scanner noise. An image object in the video imagery is linked to the audio signal, so as to distract the patient's attention away from the scanner noise. The audio-video scenery may be switched according to an estimated scanner noise level. An effective distraction of the patient is obtained with a limited audio signal level which is far lower than the scanner noise.

14 Claims, 3 Drawing Sheets

(51) Int. Cl.
*A61B 5/055* (2006.01)
*A61B 5/00* (2006.01)
*G01R 33/28* (2006.01)
*A61M 21/00* (2006.01)

(52) U.S. Cl.
CPC ............ *A61M 21/02* (2013.01); *G01R 33/283* (2013.01); *A61M 2021/005* (2013.01); *A61M 2021/0016* (2013.01); *A61M 2021/0022* (2013.01); *A61M 2021/0027* (2013.01); *A61M 2205/3375* (2013.01); *G01R 33/288* (2013.01)

(56) References Cited

OTHER PUBLICATIONS

Aliakseyeu et al. 2009 Undisturbed Sleep: Evaluation of the perceived effectiveness of sound masking. PR-TN 2009/00228.

[Ulrich et al. 2008. A Review of the Research Literature on Evidence-Based Healthcare Design. Healthcare Leadership White Paper Series 5. Georgia Institute of Technology.

SYSTEM AND METHOD FOR DISTRACTION OF PATIENT DURING SCANNING

FIELD OF THE INVENTION

The present invention relates to the field of systems and methods for improving the hospital environment experienced by a patient. More specifically, the invention relates to a system and a method aimed at reducing patient anxiety in a medical environment, such as when the patient is situated in a Magnetic Resonance (MR) imaging scanner.

BACKGROUND OF THE INVENTION

Patients that undergo MR scans are often highly stressed. The level of anxiety experienced by the patient can be rooted in the nature of the individual but is often also accentuated by other factors related to the scan. A factor that often increases the anxiety level of the patient undergoing a scan is the feeling of confinement in the MR tunnel. The long, narrow tunnel, which is required to develop a sufficiently high gradient field can induce claustrophobia type symptoms in patients who may have no previous experience of the phobia. It is estimated that more than 10% of MR scans have reduced quality due to motion artifacts induced by the nervous movements of the patient [Dantendorfer K., A study of the effects of patient anxiety . . . in magnetic imaging Magnetic Resonance Imaging Vol 15 (3) pp 301-306 1997 series 5].

While the MR tunnel is often cited as the dominant cause of anxiety another factor that increases anxiety is the excessive noise level that emanates from the scanner coils during the scan procedure. In contrast to the narrow tunnel, which has been improved by "open bore machines", the noise level has remained at nearly the same level for several generations of scanners. Currently, various solutions are offered to create an environment which is conducive to lowering the anxiety level of the patient in the MR-room.

WO 2005/051471 A1 by Philips discloses an example of a solution which includes a video being projected onto the wall and various LED lighting solutions that create an environment that is designed to relax the patient. This solution also includes other features such as rounded room corners to make the room appear seamlessly large and a design ethic that minimizes clutter and non-esthetic distractions. The patient is also given the feeling of control over his environment during the scan by being allowed to choose which theme is played during the scan: the theme being a collective name for the audio-video and lighting effects that are played during the scan. To reduce the impact of scanner noise on the patient experience, he/she is given air earphones that can supply music of choice. Since, however, the scanner noise is extremely high, in fact close to that permitted without damaging the ear, the masking of the scanner noise with music is not effective.

SUMMARY OF THE INVENTION

It would be advantageous to provide a system and a method to further increase patient comfort and reduce patient anxiety when subjected to a medical environment, such as when the patient is placed in a noisy and confining MR scanner.

In a first aspect, the invention provides a system for reducing anxiety of a patient during medical scanning procedure in an associated medical scanner device creating scanner noise, the system comprising a processor arranged to receive a measure of variation in a parameter of the scanner noise during the medical scanning procedure, and arranged to generate output signals to associated audio and video playback units so as to present an audio signal and a video imagery to the patient in accordance with the measure of variation in the parameter of the scanner noise during the medical scanning procedure, wherein an image object in the video imagery is linked to the audio signal, so as to distract the patient's attention away from the medical scanning procedure.

Such a system is advantageous since rather simple means can be used to significantly reduce patient anxiety by distracting the patient's attention away from any high anxiety moments during the medical scanning procedure. The system is based on insight of cognitive diversion, i.e. the principle of congruent multisensory stimuli for attentional control [Van Ee et al. (2009). Multisensory Congruency as a Mechanism for Attentional Control over Perceptual Selection. Journal of Neuroscience 29(37):11641-11649] and sound masking [Aliakseyeu et al. 2009 Undisturbed Sleep: Evaluation of the perceived effectiveness of sound masking. PR-TN 2009/00228], to effectively distract a patient from stressing confinement feeling and noise of a medical scanner device, e.g. an MR scanner. Due to the multi-sensorial stimulus, audio and video, then the patient is distracted away from the scanning procedure, and thus e.g. the patient perceives the supplied audio signal to be dominant over the noise of the scanner, even though it is actually of a lower level. This method of multisensory congruency [Van Ee et al. (2009). Multisensory Congruency as a Mechanism for Attentional Control over Perceptual Selection. Journal of Neuroscience 29(37):11641-11649] offers the opportunity of masking the scanner noise which, due to its almost dangerously high level, cannot be simply masked by supplying a high volume audio signal. In this context, auditive and visual inputs are linked, e.g. a dominant feature of the audio signal being a humming sound which is linked to an image object in the video imagery in the form of a humming bird flying in a nature scene. This attracts the patient's attention towards this particular auditive and visual event and distracts from the simultaneous high acoustic level from the medical scanner device, even though the scanner noise will typically be much louder than the audio signal presented. By utilizing a measure of the variation in a parameter, e.g. sound pressure level, of the scanner noise, the distraction level can be further increased, since periods with low scanner noise levels can be used to switch the audio and video presentation to create a completely different scenery for the patient, especially to a scenery with a low audio signal level, switching back to a higher audio signal level to at least partially mask the scanner noise in periods where the scanner noise is loud.

Preferably, the link between the image object in the video imagery and the audio signal is provided by the audio signal comprising sound corresponding to a sound normally associated with the image object.

Thus, the invention utilizes a characteristic inherent for the operation of e.g. an MR scanner which operates in bursts with the noise generating coils active, and these bursts are separated by silent breaks when the noise generating coils are switched off. Thus, in MR scanner noise, at least one parameter of the scanner noise varies during the medical scanning procedure. By the use of the combined effect of a scenery with linked audio and video presentations which vary in accordance with the scanner noise, it is possible to distract the patient's attention away from the scanner noise, and thus reduce the patient's level of anxiety, even though it is not possible (or desirable since it may be damaging to the patient's hearing) to present an audio signal which can completely mask the loud scanner noise.

With respect to an MR scanner, a dominant measure of variation of the noise is the noise level, i.e. the scanner noise sound pressure level. However, other dominant parameters of noise may vary for other types of scanners, e.g. changes in scanner noise spectral content or changes in temporal behavior of the noise, e.g. from stationary to impulsive noise. Thus, the audio signal and video imagery may likewise be varied according to such other parameters.

Preferably, of course, the audio signal has a high power level which at least partly overlaps with respect to dominating frequency content with the frequency content of the scanner noise, so as to obtain as high acoustic masking as possible. However, according to the invention, it is possible to reduce patient anxiety with a rather low level of audio signals, which again is more pleasant for the patient, and which relaxes the technical demands on the audio equipment used for the audio presentation.

The audio signal may be presented by means of headphones, however loudspeakers arranged inside or outside the medical scanner may also be used. The video imagery may be presented by means of a flat screen, e.g. mounted on a surface in the room, or by means of an image projector mounted inside or outside the medical scanner.

In one embodiment, said parameter of the scanner noise comprises a sound pressure level of the scanner noise during the medical scanning procedure, and wherein a parameter of the audio signal is varied in accordance with variation of the sound pressure level of the scanner noise during the medical scanning procedure. Especially, a sound pressure level of the audio signal may be varied in accordance with the variation of the parameter of the scanner noise during the medical scanning procedure, preferably such that the sound pressure level of the audio signal follows the sound pressure level of the scanner noise up and down in level. This may be implemented by switching between two different audio sequences, $S_1$ and $S_2$—one sound with a low acoustic level, $S_1$ and one another type of sound with a higher acoustic level, $S_2$. However, it may also be implemented by a simple level adjustment of one rather stationary sound, e.g. the sound of a hummingbird or bee. Varying the sound pressure level of the audio signal in accordance with variation of the sound pressure level of the scanner noise allows a high distraction of the patient, since variation or breaks in the scanner noise can in this way be utilized to introduce level variation in the audio signal without losing the acoustic masking effect.

In some embodiments, the processor is arranged to receive a measure of variation of the parameter of the scanner noise in the form of: a trigger signal indicating when a noise generating operation of the scanner is active during the medical scanning procedure, an input signal indicating a level of the scanner noise during the medical scanning procedure, or an input signal indicating a level of vibration of a part of the associated medical scanner device. All of the mentioned inputs are "on the fly" inputs which are preferably used by the processor to provide an audio and video presentation which is temporally synchronized with the scanner noise, such that periods with low scanner noise levels are utilized to switch to another audio-video event, and thus introduce an event change which serves to distract the patient during the impending high acoustic level part of the scanning procedure. The trigger signal may be provided directly from the medical scanner equipment e.g. giving a signal 1 or 2 seconds in advance of a period with a high noise level, thus allowing the system to prepare or gradually switch to another audio-video scenery. Alternatively, the trigger signal may be generated by means of equipment applied to the medical scanner device. A microphone system or accelerometer system may be used to generate an indirect "on the fly" input to the system regarding the scanner noise variation. The "on the fly" type of input may be preferred for scanners with a small degree of predictability, or for system suited to fit a large variety of scanners where the noise level cannot be predetermined.

In other embodiments, the processor is arranged to receive a measure of variation of the scanner noise in the form of one of: a predetermined estimate of temporal evolution of the scanner noise during the medical scanning procedure, a user input indicating a predetermined type of scanning, a signal input from the associated medical scanner device indicating a type of scanning. In these types of input, the system can prepare a predetermined audio-video sequence for the entire medical scanning activity before the start of scanning, since all of these inputs can be used to estimate how the variation of the scanner noise will be. The type of scan may be used by the system to select one of a prestored sets of scanner noise variations, and thus accordingly, a suitable audio-video sequence can be selected—either from pre-stored sequences or in the form of one or more parameters to be varied according to a predetermined temporal pattern so as to match the scanner noise variation. Such input types allow very simple playback systems which only receive a simple measure of variation of the parameter of the scanner noise, e.g. a short code indicating the specific type of scan, where the system then simply retrieves in response one of a number of predetermined audio-video sequences for playback suited for the specific type of scan. Especially, the processor may be arranged to increase a level of the audio signal prior to a period where a high level of the scanner noise is expected based on the measure of variation of the scanner noise. Hereby it is utilized, that the scanner noise variation, e.g. start time of a high acoustic level period, is known on beforehand, thus allowing e.g. a gradual increase in audio level starting a few seconds before the period with a high scanner noise level. Alternatively, the knowledge of an impending high acoustic level period may be used to switch to another audio-video scenery just ahead of the actual loud period, such that the patient distraction level is at the highest possible level when the loud period starts.

The processor may be arranged to select an audio signal and a video imagery in accordance with the measure of the variation of the parameter of the scanner noise by means of a predetermined selection algorithm. Hereby the system can be implemented with a simple processor, since the processor task is a simple selection. E.g. the processor may, according to the actual scanner noise variation, select between a number of pre-stored audio and video sequences or combined audio-video sequences which are found to best match the actual noise variation. This may both be done in case of "on the fly" input of scanner noise variation, or in the case where the scanner noise variation is known in advance of the medical scanning procedure. In a simple embodiment only two pre-stored audio-video sequences are used for presentation: one is selected for silent periods and another one is selected for loud periods. A simple switching between these can be done in response to a scanner noise level input, wherein the processor runs a selection algorithm comparing the received noise level input with a preselected threshold and thereby determines which of the two sequences to play.

Alternatively, the processor may be arranged to vary at least one parameter of a predetermined audio sequence in accordance with the measure of the variation of the parameter of the scanner noise by means of a predetermined variation algorithm. Especially, the processor is arranged to vary a playback level of the predetermined audio sequence in accordance with a measure of level variation of the scanner noise during the medical scanning procedure. In a simple embodiment, a pre-stored combined audio-video sequence can be used, and wherein only the level of the audio signal is adapted in accordance with the scanner noise, preferably such that the audio signal level is high in periods with loud scanner noise, and vice versa. Such embodiments are simple, and yet allow easy adjusting and adaptation to the scanner noise with the use of only a limited number of different audio-video sequences.

In one embodiment, a dominant feature in the audio signal is linked with respect to connotation to a first object arranged to move in the video imagery, e.g. the sound being a humming and the first object being a flying bee, such as mentioned. The fact that the object associated with the dominant part of the sound is moving further increases the attraction level of the patient towards the audio-video scenery presented. The first object in the video imagery may be accompanied by a second object also arranged to move in the video imagery and which is arranged to move at a lower speed than the first object. E.g. a nature scenery with a blue sky and a white cloud slowly moving in one direction. This has a relaxing effect on the patient, while e.g. the flying humming bee moves at a much higher speed and changes direction rapidly, thus keeping the patient's attention towards the moving object which is linked to the audio signal.

In some embodiments, the system may be arranged to receive an input indicating a preferred type of audio signal or video imagery to be presented. This may be an input reflecting a wish of the patient, e.g. selection between a number of pre-determined audio-video themes so as to match the preferences of the patient, which will further help to increase patient comfort and well-being. Especially, such themes may include special themes suitable for children. The choice of themes may include choice of dominant color in the video imagery.

The medical image scanner device may be a Magnetic Resonance Imaging (MRI) scanner, which has a characteristic variation in its noise, especially sound pressure level but also other parameters of the noise may vary, during a medical scanning procedure, and thus which can therefore profit from the system according to the present invention taking such variation into account. Patient anxiety can be reduced and thus patient comfort can be increased. Further, a lower patient anxiety also leads to increased scanning image quality since the patient will be less inclined to move due to anxiety movements. It is understood, however, that the invention may also be used in connection with other types of medical scanners e.g. PET-MR, PET-CT, SPECT etc. where patient anxiety is a problem.

The effect of multi-sensory distraction can be further utilized, in case the described audio and video signals are further linked to one or more additional sensory inputs including other modalities. Preferably, such additional sensory inputs being linked to the audio and video content, e.g. in the form of a further sensory input being a tactile input, or a scent which is linked to the audio-video scenery. In a specific example, the audio-video scenery may be a forest with wind and rain making noise when blowing and dropping on leaves of trees. A tactile addition to this scenery may be a provided by a fan generating a gentle wind blowing towards the face of the patient, and a scent generating device may generate a smell of "wet forest" to the patient.

In a second aspect, the invention provides a method for reducing anxiety of a patient during a medical scanning procedure in an associated medical scanner device creating scanner noise, the method comprising receiving a measure of variation in a parameter of the scanner noise during the medical scanning procedure, and generating output signals to associated audio and video playback units so as to present an audio signal and a video imagery to the patient in accordance with the measure of variation in the parameter of the scanner noise during the medical scanning procedure, wherein an image object in the video imagery is linked to the audio signal, so as to distract the patient's attention away from the scanning procedure.

In a third aspect, the invention provides a computer executable program code arranged to perform the method according to the second aspect.

It is appreciated that the same advantages and embodiments of the first aspect apply as well for the second and third aspects. In general the first, second, and third aspects may be combined and coupled in any way possible within the scope of the invention. These and other aspects, features and/or advantages of the invention will be apparent from and elucidated with reference to the embodiments described hereinafter.

The invention may be implemented in several ways. In some implementations the system is in the form of a stand-alone device which is arranged to supplement an existing medical scanner system, e.g. a full stand-alone system including audio and video presentation means. Alternatively, the system may be partly or fully integrated with a medical scanner system, e.g. with the system according to the invention being in the form of software, e.g. software forming an integrated part of the software controlling the medical scanner device, and thus utilizing at least one processor which is already present in a medical scanner system. Alternatively, the system according to the invention may form part of a system controlling environmental factors in and around the medical scanner room, such as controlling ambient lighting and sound, with the purpose of enhancing patient comfort.

BRIEF DESCRIPTION OF THE DRAWINGS

Embodiments of the invention will be described, by way of example only, with reference to the drawings, in which.

DESCRIPTION OF EMBODIMENTS

Figure 1:
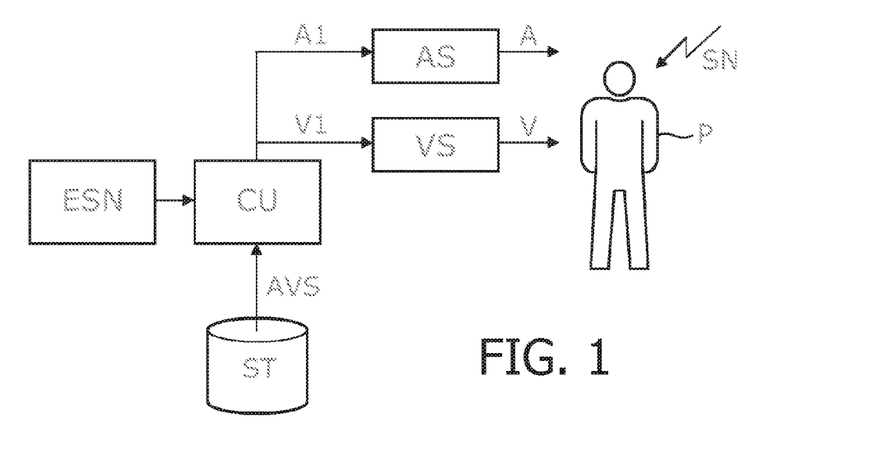
FIG. 1 shows a diagram of a system embodiment of the invention.

FIG. 1 illustrates in diagram form basic elements of a system for reducing anxiety of a patient P during a medical scanning procedure in a medical scanner device which creates a disturbing and unpleasant scanner noise SN. An example of such a medical scanner device is an MRI scanner. The system comprises a control unit CU with a processor. The processor is arranged to receive, in this embodiment, a measure of variation in a parameter of the scanner noise SN in the form of an estimate of a parameter of the scanner noise ESN during the medical scanning to be performed. This estimate of the scanner noise ESN may be applied to the system from outside, or the estimate may be generated by an algorithm in the system itself, e.g. based on an input informing the system of the type of scan to be performed, thus allowing a predetermined algorithm or a simple selection algorithm to determine e.g. the temporal evolution of the scanner noise SN level during the scan. This allows the processor to select proper video imagery and a linked audio signal AVS, e.g. by retrieving proper AV files stored at a server or at a local hard disk ST, as illustrated in FIG. 1. A number of AV files may be stored to allow a simple selection of the AV file to be retrieved from the AVS, once the type of scan (one among a limited number of types) is known. Hereby, it is a simple task for the control unit CU to generate AV output signals A1 and V1 and to supply these to the respective audio and video systems AS, VS, so as to present the desired audio signal A and video imagery V to the patient P in the medical scanner room during the scanning procedure.

The control unit CU may also select between different stored AV files from the AVS in accordance with the estimated scanner noise SN variation, e.g. such that one AV sequence is selected in silent periods, while another one is selected when the estimated scanner noise SN level exceeds a predetermined threshold. More alternatively, one sequence may be selected, and then the audio signal A1 level is adjusted to follow the estimated scanner noise SN level.

The control unit CU may have a trigger input which inform the control unit CU then the medical scanning starts, thus allowing the played scenery A, V to be synchronized with the variation of the actual scanner noise SN during the scanning sequence. Hereby, it is possible to obtain that the audio signal and video signal A, V are presented in accordance with the estimated measure of variation in the scanner noise SN during the medical scanning procedure.

To provide the desired distraction to the patient P from the scanner noise SN, the audio signal output A1 and the video imagery output V1 are linked with respect to content, such that an image object in the video imagery V is linked to the audio signal A. This link may be provided e.g. if the audio signal output A1 has a dominant part which corresponds to the sound normally associated with an object shown in the video imagery output V1 at the same time. The link between audio A and video V has the effect that the patient P perceives the audio signal A clearly and focuses on the specific audible features therein due to the fact that these audible features are associated with a known image object in the video imagery V presented at the same time. Thus, even though the simultaneous scanner noise SN is clearly dominating with respect to measurable sound pressure level, the patient P will be distracted away from the scanner noise SN and towards the audio signal A via the clear link with respect to content. The effect is that the patient P is distracted from the unpleasant feeling of being placed in the scanner, and instead focuses attention towards the presented audio-visual scenery A, V.

Most preferably, the image object linking audio A and video V is selected to most likely be perceived as pleasant by the patient P, e.g. an element from nature, such as an animal, ocean waves, noise from wind blowing in leaves on a tree or the like. Even more preferably, the object is selected such that its sound has a dominating frequency content which overlaps the dominating frequency content of the scanner noise SN, thus allowing a reasonable degree of acoustic masking of the scanner noise, even though the level of the audio signal A presented to the patient is significantly lower than the noise SN generated by the scanner. E.g. in case the scanner noise SN is dominated by tonal components, the audio signal A may be selected to include the same tonal components. Further, in case the scanner noise SN is dominated by a special temporal noise components such as impulsive or beating or other periodic characteristics, the audio signal A may likewise be selected to coincide with such temporal features in the scanner noise SN.

In the following examples of further features that may be applied so as to provide an audio-video scenery A, V that further distraction the attention of the patient P away from the medical scanning procedure. It is to be understood, that these further features may be combined in any way.

In one embodiment a combination of nature imagery (which is known to relax patients [Ulrich et al. 2008. A Review of the Research Literature on Evidence-Based Healthcare Design. Healthcare Leadership White Paper Series 5. Georgia Institute of Technology]), is used in combination with a high density audio signal. An example of such a combination could be a video image showing a hummingbird with the audio including the sound of beating of wings, a video showing a jungle scene and with audio including the noise of rain on leaves, or a video with an ocean scene where the audio includes the sound of crashing waves (the latter two sound types have already proven to be effective masking sounds [Aliakseyeu et al. 2009 Undisturbed Sleep: Evaluation of the perceived effectiveness of sound masking. PR-TN 2009/00228]).

Figure 2:
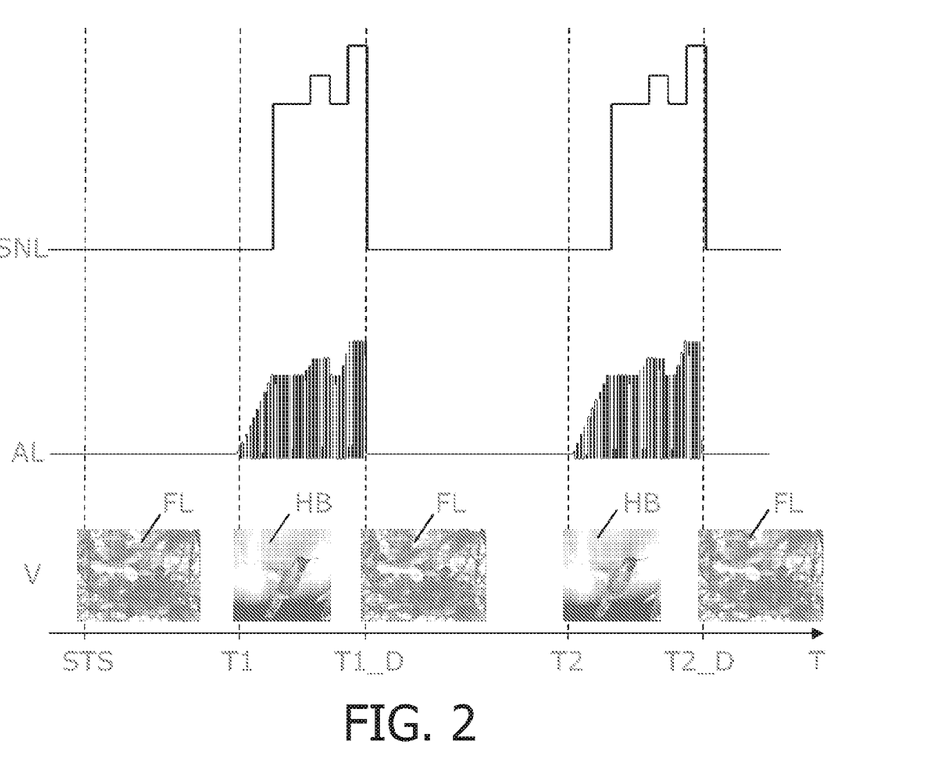
FIG. 2 illustrates examples of video clips and the level of the corresponding audio output in response to scanner noise level.

FIG. 2 illustrates an example of the parameter being scanner noise level SNL, e.g. expressed as sound pressure level, as well as level AL, e.g. also sound pressure level, of the presented audio signal T and the selected video signal V versus time T. The presented audio-video scenery is adapted to follow the temporary evolution of the scanner noise in the form of both audio signal level AL and video signal V being varied in accordance with the level SNL of the scanner noise. As seen, the scanner noise level SNL varies significantly with time T, which is typical for an MR scanner which normally has a menu of pre-programmed scan routines and the scanner noise level SNL versus time associated with each routine is thus easily predictable. As seen in the example, the same noisy sequence is repeated with intermediate breaks. This is utilized in the audio-video presentation to switch between two audio-video sceneries: 1) when the scanner noise is low, and 2) during a noisy scanning sequence.

When the scanner noise is low (silent periods, i.e. between scanner start time STS and T1, between T1_D and T2, and after T2_D), a video FL being a panning view of the flowers that hummingbird feeds on. The flower video FL is presented along with the audio signal being either switched off or being at a very low background level, e.g. birds singing which is linked to the flower FL video. Shortly before onset of the noise scanning sequences, at times T1, T2, the audio and video scenery is switched to a video showing a close up video of a hummingbird HB and an audio signal being the noise from the hummingbird wings. As seen, the audio signal level AL is ramped up from a very low level to a high level before onset of the scanner noise, and thus the patient will experience a pleasant transition from the silent or almost silent period with the audio attention solely on the hummingbird wing sound before the scanner noise level SNL becomes high. Hereby the patient's attention is distracted towards the just switched audio-visual scenery and thus helping to suppress the experience of the unpleasant scanner noise. Even though the presented hummingbird wing sound has a much lower level than the scanner noise, it is seen that the level of the sound is selected to follow also smaller variations in the scanner noise level SNL versus time, thus further providing the feeling that the audio-video scenery is the primary impression factor for the patient who then suppresses the fact that the scanner noise level SNL actually also has peaks at the same time where the humming bird sound level AL also has its peaks. Further, this means that the level of the hummingbird wing sound relative to the scanner noise is perceived to be almost steady.

Figure 3:
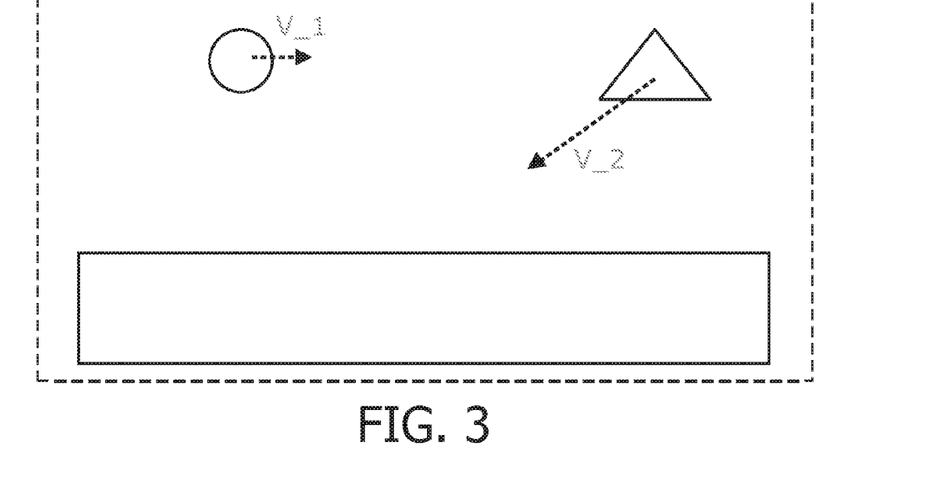
FIG. 3 illustrates in schematic form a video clip with two image objects moving at different velocity.

FIG. 3 illustrates a sketch of a video imagery within the dashed rectangular box showing the principle which can help to further catch the patient's attention towards the presented audio-video scenery. FIG. 3 illustrates three image objects of the video imagery: a steady rectangular object in the bottom, and two moving objects: a circle and a triangle which move at different speeds and in different directions, which is indicated by the dashed velocity vectors V_1, V_2 indicated for the objects. The fact that two image objects move at different speed helps to distract the patient, since the slowly moving object helps to make the patient relax, while the object moving fast attracts immediate attention. Especially, the object moving fast may be linked to the audio presentation, or the audio presentation may include audible features that are linked to both of the slow and fast image objects.

Figure 4:
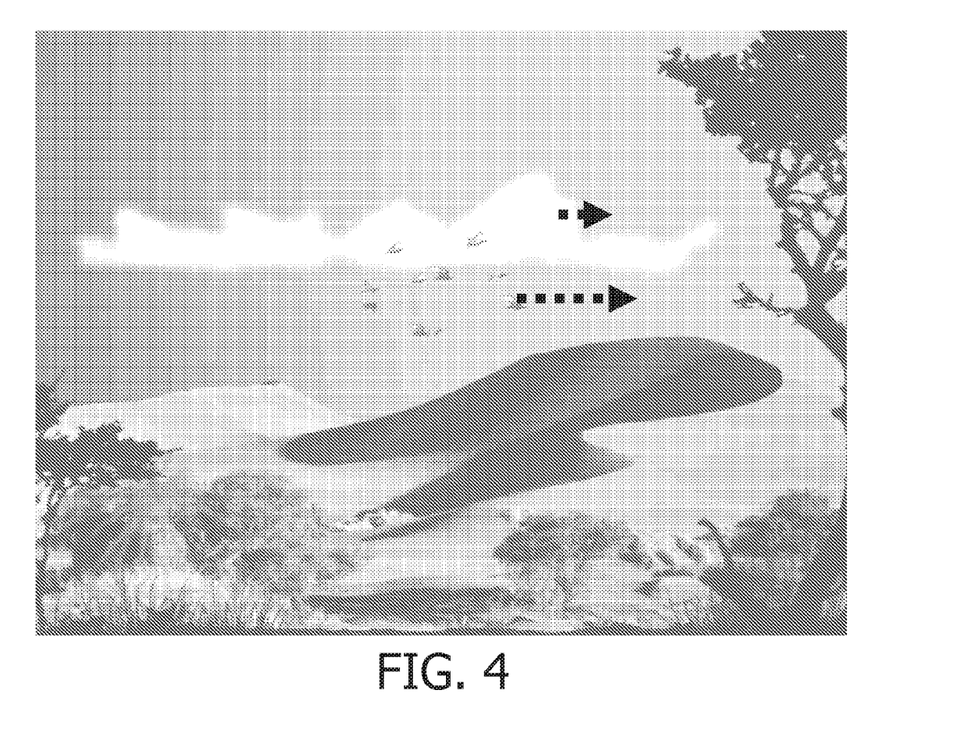
FIG. 4 illustrates a video clip showing two moving image objects, namely a cloud and flying birds.

FIG. 4 shows a concrete imagery utilizing the principle of FIG. 3, namely a video with a nature scenery in the form of a steady landscape with trees and bushes and a blue sky with slowly moving white clouds (velocity indicated by the short dashed arrow). In addition, a flock of birds are flying across the scenery in the same direction as the clouds, from left side towards the right side of the image, but at a much higher speed (long dashed velocity arrow) than the clouds. In such a scene then the clouds create a relaxing ambience while the birds prevent the patient losing attention and a drifting of their thoughts. If, however, the flock of birds is repeated too often, then this motion also loses effectiveness. It is therefore more effective to limit the use of the high speed motion component and instead only trigger this component when a high scanner noise is imminent. Again, due to the fact that the scans are pre-programmed then the scanner noise is predictable and can be anticipated to render the theme video.

While the noise of a medical scanner is often predictable (at least if the scan procedure is known), there are cases where it is preferred not to have communication between the scanner and the distraction system arranged to increase patient comfort. This can be related to regulations regarding interactions with a medical device. If this is the case, then a microphone can be placed in the scanner room. The microphone is connected to the control unit, e.g. a computer, and the scanner noise is recorded and analyzed. The control unit is in connection with a server which is equipped with real-time software that matches the initial scan noise with a pre-programmed look-up table and generates an expected sound profile for the rest of the scan. This profile is then used for coordinating the audio-visual distraction system. Alternatively, the software can be self-learning and compare the current noise profile to previous noise profiles. When a match is found, then the previous sound profile is used to co-ordinate the current audio-visual presentation of the distraction system.

In yet another embodiment, music is used as the primary distractor. The video stimulation is rendered on the basis of the audio stream using on-the-fly beat- and soundwave detection to generate a video stream of abstract visual effects that is in synchronized with the music. The co-ordination between music and video can be either continuous, or only when peaks in scanner noise are expected. The use of on-line video rendering algorithms will permit any audio material to be used, so this can also be music that the patient brings to the hospital.

Figure 5:
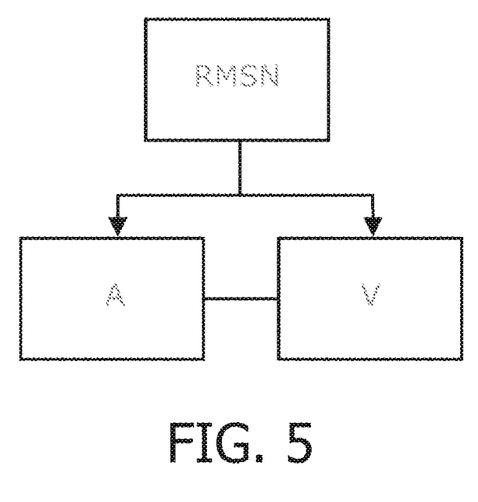
FIG. 5 illustrates in diagram form a method embodiment.

FIG. 5 illustrates the method for reducing anxiety of a patient during medical scanning in an associated medical scanner creating scanner noise according to the invention. First, a measure of variation in the scanner noise during the medical scanning procedure is received RMSN. This may include receiving a simple input regarding one of a predefined number of scans to be performed thus allowing an estimation or prediction of expected scanning noise versus time during the medical scanning procedure. Alternatively, the scanning noise is recorded and analyzed on-line to derive a measure of variation in the scanner noise. Based on the measure of variation in the scanner noise, output signals to associated audio and video playback units are generated, A and V. These output signals are generated so as to present an audio signal and a video imagery to the patient in accordance with the measure of variation in the scanner noise during the medical scanning procedure. Further, these output signals are generated such that an image object in the video imagery is linked to the audio signal, so as to distract the patient's attention away from the scanning procedure, and thus also from the scanner noise.

It is to be understood that the present invention may be used as part of complete patient comfort systems, such as the Ambient Healing Environment™ or Ambient Experience™ systems by Philips, which include ambient lighting and sound effects and other features for improving medical environments so as to increase patient well-being.

To sum up, the invention provides a system and method for reducing anxiety of a patient during medical scanning in a medical scanner which may produce significant levels of acoustic noise. A processor or control unit CU receives a measure of variation ESN in a parameter of the scanner noise SN during the medical scanning, e.g. estimated scanner noise level based on the actual type of scanning. The processor then generates outputs A1, V1 to audio and video playback units AS, VS that accordingly present an audio-video scenery A, V to the patient during the scanning, in accordance with the measure of variation ESN in the parameter of the scanner noise SN. An image object, e.g. a moving image object, in the video imagery V is linked to the audio signal A, so as to distract the patient's attention away from the scanner noise SN. The audio-video scenery A, V may be switched according to an estimated scanner noise level, e.g. a switch between two different scenes: one for noisy scanning periods, and another one for silent periods. An effective distraction of the patient is obtained with a limited audio signal A level which is far lower than the scanner noise SN.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system for reducing anxiety of a patient during a medical scanning procedure in a medical scanner device creating scanner noise, the system comprising a processor
arranged to receive a measure of variation in a parameter of the scanner noise during the medical scanning procedure, and
arranged to generate output signals to audio and video playback units so as to present an audio signal and a video imagery to the patient in accordance with the measure of variation in the parameter of the scanner noise during the medical scanning procedure, wherein an image object in the video imagery is linked to the audio signal, so as to distract the patient's attention away from the scanning procedure,
wherein the processor is arranged to receive a measure of variation in the parameter of the scanner noise in the form of one of: a predetermined estimate of temporal evolution of the scanner noise during the medical scanning procedure, a user input indicating a predetermined type of scanning, a signal input from the medical scanner device indicating a type of scanning, and wherein the processor is arranged to increase a sound pressure level of the audio signal prior to a period where a high sound pressure level of the scanner noise is expected based on the measure of variation of the parameter of the scanner noise.

2. System according to claim 1, wherein said parameter of the scanner noise comprises a sound pressure level of the scanner noise during the medical scanning procedure, and wherein a parameter of the audio signal is varied in accordance with variation of the sound pressure level of the scanner noise during the medical scanning procedure.

3. System according to claim 1, wherein a sound pressure level of the audio signal is varied in accordance with the variation in the parameter of the sound pressure level of scanner noise during the medical scanning procedure.

4. System according to claim 1, wherein the processor is arranged to receive a measure of variation in the parameter of the scanner noise in the form of one of: a trigger signal indicating when a noise generating operation of the scanner is active during the medical scanning procedure, an input signal indicating a level of the scanner noise during the medical scanning procedure, an input signal indicating a level of vibration of a part of the medical scanner device.

5. System according to claim 1, wherein the processor is arranged to select an audio signal and a video imagery in accordance with the measure of the variation of the parameter of the scanner noise by means of a predetermined selection algorithm.

6. System according to claim 1, wherein the processor is arranged to vary at least one parameter of a predetermined audio sequence in accordance with the measure of the variation of the parameter of the scanner noise by means of a predetermined variation algorithm.

7. System according to claim 6, wherein the processor is arranged to vary a playback level of the predetermined audio sequence in accordance with a measure of sound pressure level variation of the scanner noise during the medical scanning procedure.

8. System according to claim 1, wherein a dominant feature in the audio signal is linked with respect to connotation to a first object arranged for moving in the video imagery.

9. System according to claim 8, wherein the video imagery comprises a second object arranged for moving in the video imagery which is arranged to move at a lower speed than the first object.

10. System according to claim 1, arranged to receive an input indicating a preferred type of audio signal or video imagery to be presented.

11. System according to claim 1, wherein the medical scanner device is a Magnetic Resonance Imaging scanner.

12. System according to claim 1, wherein the sound pressure level of the audio signal is lower than the sound pressure level of the scanner noise.

13. Method for reducing anxiety of a patient during a medical scanning procedure in an associated medical scanner device creating scanner noise, the method comprising
receiving a measure of variation in a parameter of the scanner noise during the medical scanning procedure, and
generating output signals to associated audio and video playback units so as to present an audio signal and a video imagery to the patient in accordance with the measure of variation in the parameter of the scanner noise during the medical scanning procedure, wherein an image object in the video imagery is linked to the audio signal, so as to distract the patient's attention away from the scanning procedure.

14. A non-transitory computer readable storage medium comprising a computer program wherein the computer readable program when executed on a computer causes the computer to perform a method for reducing anxiety of a patient during a medical scanning procedure in an associated medical scanner device creating scanner noise, the method comprising
receiving a measure of variation in a parameter of the scanner noise during the medical scanning procedure, and
generating output signals to associated audio and video playback units so as to present an audio signal and a video imagery to the patient in accordance with the measure of variation in the parameter of the scanner noise during the medical scanning procedure, wherein an image object in the video imagery is linked to the audio signal, so as to distract the patient's attention away from the scanning procedure.

* * * * *